US005700476A

United States Patent [19]

Rosenthal et al.

[11] Patent Number: 5,700,476
[45] Date of Patent: Dec. 23, 1997

[54] HETEROMORPHIC SPONGES CONTAINING ACTIVE AGENTS

[75] Inventors: Arthur L. Rosenthal, Arlington, Tex.; Nicholas D. Light, Doune; Carla A. Haynes, Cambuslang, both of United Kingdom

[73] Assignee: Johnson & Johnson Medical, Inc., Arlington, Tex.

[21] Appl. No.: 393,963

[22] Filed: Feb. 24, 1995

Related U.S. Application Data

[62] Division of Ser. No. 35,013, Mar. 22, 1993, Pat. No. 5,466,462.

[30] Foreign Application Priority Data

Mar. 25, 1992 [GB] United Kingdom ............... 9206509

[51] Int. Cl.$^6$ .................... A61F 2/02; A61F 13/15; A61F 13/20; A61K 47/42
[52] U.S. Cl. ................... 424/426; 514/773; 514/774; 514/777; 514/781; 604/359; 604/360; 604/364; 604/368; 604/379
[58] Field of Search ................ 424/423, 426; 514/773, 774, 777, 781; 604/359, 360, 364, 368, 369, 379

[56] References Cited

U.S. PATENT DOCUMENTS

| | | | |
|---|---|---|---|
| 3,823,212 | 7/1974 | Chvapil | 264/49 |
| 4,233,360 | 11/1980 | Luck et al. | 424/443 |
| 4,320,201 | 3/1982 | Berg et al. | 435/265 |
| 4,614,794 | 9/1986 | Easton et al. | 530/356 |

FOREIGN PATENT DOCUMENTS

| | | |
|---|---|---|
| 0 042 253 | 12/1981 | European Pat. Off. . |
| 0246638 | 11/1987 | European Pat. Off. . |
| 0 314 109 | 5/1989 | European Pat. Off. . |
| 0 403 650 | 12/1990 | European Pat. Off. . |
| 3 23864 A | 1/1991 | Japan . |
| 1 144 552 | 3/1969 | United Kingdom . |
| 2 215 209 | 9/1989 | United Kingdom . |
| WO 85/04413 | 10/1985 | WIPO . |
| WO 90/00060 | 1/1990 | WIPO . |

OTHER PUBLICATIONS

Collagen Sponge: Theory and Practice of Medical Applications; J. Biomed. Mater. Res; vol. 11, pp. 721–741 (1977); Milow Chvapil.

Design of an Artificial Skin. I. Basic Design principles; Journal of Biomedical Materials Research, vol. 14, 65–81 9 I.V. Yannas and John F. Burke.

EPO Search Report in EP 93 30 2319, a corresponding foreign application.

*Primary Examiner*—Carlos A. Azpuru
*Attorney, Agent, or Firm*—Andrew C. Farmer

[57] ABSTRACT

The invention provides wound dressing and/or implant materials comprising a matrix structure of sponge, at least one substructure and at least one pharmacologically active agent, wherein both the matrix structure and the substructure are formed from bioabsorbable biopolymer materials. The substructure may, for example, comprise biopolymer films, flakes, fibres or microspheres embedded in the matrix structure of sponge. The pharmacologically active agent may comprise antiseptics, antibiotics, analgesics. One or more such active agents may be incorporated separately into the matrix and/or the substructure so as to achieve controlled or phasic release of the active agents into the wound.

7 Claims, No Drawings

HETEROMORPHIC SPONGES CONTAINING ACTIVE AGENTS

This is a divisional of application Ser. No. 08/035,013 filed Mar. 22, 1993, now U.S. Pat. No. 5,466,462 which is hereby incorporated by reference.

The present invention relates to bioabsorbable wound implant materials, and more particularly to heteromorphic sponge materials containing one or more pharmacologically active agents, which are suitable for use as implantable materials in wound repair.

Porous materials formed from synthetic and/or naturally occurring bioabsorbable materials have been used in the past as wound dressings or implants. The porous material provides structural support and a framework for tissue ingrowth while wound healing progresses. Preferably, the porous material is gradually absorbed as the tissue around the wound regenerates.

Typical bioabsorbable materials for use in the fabrication of porous wound dressings or implants include synthetic bioabsorbable polymers such as polylactic acid or polyglycolic acid, and also biopolymers such as the structural proteins and polysaccharides. The structural proteins include collagen, elastin, fibronectin, laminin and fibrin, as well as other proteins of the human connective tissue matrix. Of these, the most studied material has been collagen.

Collagen is the most abundant animal protein and the major protein of skin and connective tissue. A high degree of homology exists between the various types of collagen found in different animal species and human collagen. Accordingly, animal collagen types such as bovine collagen are useful because they exhibit very low immunogenicity when implanted into humans or used as topical dressings on human wounds.

Collagen may be prepared in a variety of physical forms including fibres, flakes, films or aqueous gels. Freeze drying an aqueous gel or an aqueous suspension of collagen may be used to produce a porous collagen sponge. Collagen sponges are described, for example, in Chvapil, J. Biomed. Mater. Res. 11 721–741 (1977). The use of collagen sponges and/or other freeze-dried biopolymer sponges as wound dressings or implant materials is disclosed, for example, in U.S. Pat. No. 4,614,794 and U.S. Pat. No. 4,320,201.

High molecular weight polysaccharides of the mammalian connective tissue matrix have also been used in various types of wound dressing or "synthetic skins". Yannas I. V. & Burke, J. F., J. Biomed. Mater. Res. 14 56–81 (1980) describe the use of such polysaccharides in wound dressings formed by freeze drying as sponges. High molecular weight polysaccharides include such molecules as chondroitin sulphate, hyaluronic acid and dermatan sulphate.

U.S. Pat. No. 4,614,794 describes the use of other naturally occurring polysaccharide materials, especially of plant origin, in the dressing of wounds. These include, for example, alginates, chitosan, chitin, guar gum, and various plant gums.

Porous materials comprising more than one kind of bioabsorbable polymer have also been suggested for use as wound implants or wound dressings. For example:

GB-A-2215209 (Osmed Inc.) describes a biodegradable, osteogenic bone-graft substitute comprising: (a) a porous, rigid structure formed from a biodegradable polymer such as polylactic or polyglycolic acid; (b) a chemotactic substance such as hyaluronic acid, fibronectin or collagen dispersed in the interstices of the rigid structure, and (c) a biologically active or therapeutic substance such as bone morphogenetic protein evenly distributed throughout the volume of the bone-graft substitute. In use, the material is implanted into a bone defect. The material helps to restore functional architecture and mechanical integrity of the bone, initiate osteogenesis, and maintain the biological processes of bone growth while simultaneously being slowly bioabsorbed by the host organism.

JP-A-03023864 (Gunze KK) describes a reinforced collagen sponge for use as a filling material for biological tissue. The collagen sponge is reinforced by the addition of fibres of poly-(L-lactic acid). The resulting fibre-reinforced composite sponge is stronger than pure collagen or cross-linked collagen sponges, and is bioabsorbed more slowly in a host organism.

Implants made from biological, bioabsorbable components are normally intended to be invaded by the cells of the host or recipient of the implant. Cellular invasion of homogeneous sponge implants, however, is not necessarily achieved in the most efficient manner. The closed honeycomb nature of sponges presents a series of "walls" to cells invading the structure, each of which has to be breached before progress can continue. Cellular invasion is required by cells which can degrade the implant materials and by those which can lay down the tissue to replace the implant and thus repair any defect which the implant is intended to repair. Failure of either type of cell to invade the structure of the implant in an efficient manner prevents vascularization which is required for new tissue to be able to sustain its life.

Furthermore, the porous bioabsorbable implants that have been suggested to date are all isotropic materials. That is to say, the structure and composition of the materials are uniform in all directions. Any active agents for wound healing are incorporated uniformly into the existing materials. This in turn means that the active agents are released uniformly into the wound at a rate determined only by the rate at which the implant material biodegrades. In practice, it would be preferable to have controlled or phasic release of active agents. For example, an initial rapid release of the active agents to establish a sufficient concentration of those agents at the wound surface followed by the slower release required to maintain a constant concentration. Alternatively, it may be desirable to have an initial rapid release of antiseptic followed by slower release of wound healing factors such as cytokines, FGF etc.

Accordingly, it is an object of the present invention to provide a porous bioabsorbable material that is suitable for use in the repair of full and partial thickness defects of the skin and defects or deficiencies of other soft tissues. In particular, it is an object of the present invention to provide a porous material that is readily invaded by cells of the host organism and that provides for controlled or phasic release of pharmacologically active agents into the wound.

The present invention provides a bioabsorbable heteromorphic sponge comprising a matrix structure of sponge and at least one substructure, wherein the matrix and the substructure are formed of bioabsorbable materials and the sponge comprises at least one pharmacologically active agent.

The term "heteromorphic" means that the sponges according to the present invention are structurally inhomogeneous due to the presence of the substructure in the sponge matrix. The sponges according to the present invention may also be chemically inhomogeneous if the substructure has a different chemical composition than the sponge matrix. In preferred embodiments one or more active agents is incorporated separately into the matrix structure or into one or more of the substructures. More preferably, different active agents are incorporated separately in the matrix structure and in the one or more substructures. This arrangement provides for phasic release of the different active agents because, under physiological conditions, release of the active agents takes place first from the sponge matrix and then from the substructures. Moreover, because the ratio of surface area to volume of the substructures can be controlled, the rate of release of the active agents from the substructures can thereby also be controlled.

The pharmacologically active agent is preferably selected from the group consisting of: antimicrobials to control infection, cytokines and growth factors to enhance healing; antibodies to specific wound components such as TGF β to prevent contracture, peptides to act as chemotactic agents, angiogenic factors, hormones, enzymes, metabolic or breakdown products of biopolymers, pain killers or mixtures thereof.

The amount of the pharmacologically active agent that can be incorporated will depend on the physical state of the active agent, i.e. whether it is a solid, liquid or emulsion under the conditions of incorporation. The amount that can be incorporated also depends on the chemical affinity between the active agent and the biopolymer of the matrix structure or the substructure. In favorable cases, such as when the active agent is an emulsified oil distributed in a collagen matrix, up to 90% of the weight of the matrix structure or the substructure may consist of the active agent. Likewise, up to 50% by weight of the antiseptic chlorhexidine gluconate can be incorporated into a collagen-based sponge matrix or a collagen-based substructure.

The amount of the pharmacologically active agent that is actually incorporated into the heteromorphic sponges in practice will depend on the pharmacological activity and the cost of the active agent. Thus, expensive and highly active substances such as cytokines may be incorporated at the 0.1–100 ppm by weight level. On the other hand, antiseptics such as chlorhexidine gluconate are preferably incorporated at high levels such as 1–40 percent by weight.

The substructure in the heteromorphic sponge according to the present invention may be oriented. That is to say, the substructure may be anisotropic and thereby define preferred directions for cellular ingrowth into the sponge. The anisotropy is normally provided by the use of oriented flakes, films, fibres or the like to form the substructure.

The sponge is bioabsorbable in that it is capable of full degradation and resorption within a patient's body. The heteromorphic sponge is preferably used as a wound implant for example in partial or full thickness skin injury or in tissue insufficiency where soft tissues are required to be replaced.

Preferably, the matrix and the substructure are both formed from biodegradable biopolymer materials.

The matrix is preferably strong and resilient enough to resist collapse and may be cut and/or formed so as to conform to a wound shape so that it protects and/or fills a wound bed. It may, for example, be cut so as to fill the full depth of a wound or tissue deficient area.

A heteromorphic sponge which has been cut to shape can then be placed into a debrided wound bed. A wound which has a heteromorphic sponge implanted therein may then be dressed with a suitable dressing and healing allowed to take place. Regrowth of new tissue into the heteromorphic sponge enhances wound healing.

The heteromorphic sponge may allow wound fluid, oxygen and other gases to pass through the sponge and can be replaced by host tissues in such a way that healing is promoted and cosmetic damage minimized.

Preferably, the sponge matrix comprises one or more proteins or one or more polysaccharides, or a mixture of one or more proteins with one or more polysaccharides.

The sponge matrix and substructures within the matrix may include all collagen types, tenascin, laminin, chondroitin sulphate, hyaluronic acid, dermatan sulphate, heparin sulphate, heparin, elastin, fibrin, fibronectin, vitronectin, dextran, or oxidized regenerated cellulose.

In particularly preferred embodiments, the sponge matrix consists essentially of collagen. The collagen may be provided by harvesting it as a fibrous mass containing largely collagen types I and III from such animal sources as skin, tendon, intra-organ connective tissue and bone and from such species as cattle, sheep, pigs, chickens, turkeys, kangaroo, deer or other mammals.

The substructures may be formed from material which is the same material as that of the matrix or may be formed from another material. The substructure may be in the form of milled freeze-dried sponges, powders, aggregates, microspheres films, flaked or otherwise broken films, fibres, fibre bundles or mixtures of these.

The substructure may be oriented within the matrix to provide conduits or pathways for cells to follow, enabling them to invade into the body of the matrix of the heteromorphic sponge. Particularly preferred for this purpose are substructures which are elongate or flat and planar, such as films or film flakes, fibres or fibre bundles. The sponge component of the matrix thus has its homogeneous structure sufficiently interrupted by the substructures to facilitate cellular movement. Thus, endothelial cells and fibroblasts can migrate relatively rapidly in the matrix structure and begin, at an early stage after implantation, the process of degradation and renewal.

The heteromorphic sponge may be formed by making a heterogeneous premix comprising the substructure material suspended in a gel, paste, slurry or emulsion of the matrix material which is then freeze dried.

Pharmacologically active agents which are required for incorporation into the heteromorphic sponges may be added to the gel, paste, slurry or emulsion, and/or to the second components which will become substructures of the sponge before these are added to the premix for freeze drying.

Where desired, orientation of the substructure may be achieved in different ways. For example, the elements of the substructure such as films, fibres and the like may be laid down in an ordered fashion in a bath of the matrix gel, paste or slurry. Alternatively, the substructure may be an ordered structure such as a honeycomb of the substructure material which is then flooded with the matrix gel, paste, slurry or emulsion. Spontaneous ordering of the substructure can also take place. For example, where flakes of the substructure material are stirred into a slurry as above and the mixture is allowed to stand before freeze drying, spontaneous ordering of the flakes is observed in the freeze-dried product. Spontaneous ordering of flakes and fibres also occurs when pastes or gels containing these substructures are extruded.

In a preferred method, fibrous collagen, pre-washed to remove the majority of non-collagenous components as described in U.S. Pat. No. 4,614,794 or U.S. Pat. No. 4,320,201 is suspended in clean deionized pyrogen free water and homogenized to a fine fibrous suspension by passage through a homogenizing system. Suitable homogenizing systems are described in U.S. Pat. No. 4,320,201.

Homogenization may be continued until a desired degree of fibre division is achieved. This results in a preferred fibre size of between 0.01 and 10 mm.

Preferably, homogenized collagen is acidified to cause it to swell to a premix or gel suitable for freeze drying. The acidifying step may use an organic acid such as formic, acetic, propionic, lactic, malonic, or dilute inorganic acids such as hydrochloric acid at a solids content of between 0.01% and 30% to a final pH of between 2 and 6. A preferred embodiment results in a pH of between 3.0 and 4.5.

Adding pharmacologically active agents to the matrix premix or gel preferably produces a final weight concentration of between 0.001% and 50% based on the dry weight of the dried matrix material. The second components may then be mixed so as to disperse them throughout the body of the premix. Mixing usually comprises stirring and may further include adding cross-linking agents to stabilize the matrix.

A plasticizer such as glycerol or sorbitol may be added to a final concentration of between 0.1% and 5%, based on the dry weight of collagen, and mixed with the premix. Oil may also be added at this stage with adequate homogenization. The resulting matrix may comprise a slurry, gel, paste, emulsion or suspension which may then be mixed quickly with a preformed, fabricated solid material of the substructure to form the heterogeneous mix desired. This is then preferably fully degassed, poured into trays and freeze dried.

The heteromorphic sponge can be freeze dried at its desired final thickness or dried as a block and cut to size and shape prior to packaging and sterilization. Where a film is produced, this may be rolled onto tube carriers or pre-cut into lengths and stored flat. Films may also be made by pouring a slurry of collagen onto flat trays and drying in a stream of warm air at between 20° C. and 80° C.

The invention is now further described with reference to the following examples.

EXAMPLE 1

(Comparative Example)

An isomorphic single-component collagen sponge is prepared as follows.

An acetic acid suspension of collagen is prepared substantially as described above and in U.S. Pat. No. 4,614,794. The suspension is adjusted to 0.45% solids, degassed and poured into trays to a depth of 3 mm. The mixture is rapidly frozen and freeze dried. The resultant material is an isomorphic, substantially homogeneous collagen sponge.

EXAMPLE 2

(Comparative Example)

An isomorphic collagen sponge incorporating the antibacterial agent chlorhexidine gluconate (CHG) prepared as follows.

An acetic acid suspension of collagen is prepared as in Example 1 and is adjusted to 0.45% solids w/v. Chlorhexidine gluconate is added to a concentration of 53% w/w of collagen. That is to say, the total weight of chlorhexidine gluconate in the suspension is 53% of the total weight of collagen in the suspension. The suspension is degassed and freeze dried as described in Example 1. The resulting material is a strong, isomorphic, substantially homogeneous sponge material comprising approximately one third by weight of chlorhexidine gluconate.

EXAMPLE 3

A two-component heteromorphic sponge according to the present invention having chlorhexidine gluconate incorporated in both the sponge matrix and the substructure is prepared as follows.

First, a gel or slurry of collagen fibres containing 0.3% w/v of collagen is prepared as described above. Glycerol is added as a plasticizer to a final weight of 0.02% w/v.

Chlorhexidine gluconate is then added to a final weight of 0.23% w/v. The gel is then extruded through a suitable flat bed 2 mm slit extruder onto a moving belt of suitable material so as to form a fine, unbroken film on the moving belt. The moving belt passes through a drying cabinet with the temperature set at 55° C. The resulting dry film is stored by rolling onto tube carriers or as pre-cut lengths stored flat in boxes.

In a variant, the dry film is made by pouring the slurry of collagen onto flat trays and drying in a stream of warm air.

In a further variant, a thicker film is made as described above but by formulating the gel or slurry with 0.75% w/v of collagen fibres. The gel or slurry is extruded as above through a slit extruder of equal thickness setting, resulting in a film that is approximately twice as thick after drying.

The two-component heteromorphic sponge system is made by fabricating the pre-cast and dried films with sponge premix, as follows. A layer of collagen sponge gel or slurry containing chlorhexidine gluconate and prepared as in Example 2 is poured into a tray at a thickness of 1 mm and blast frozen. Collagen film prepared as above is then placed onto the frozen slurry and a second layer of collagen slurry poured over the collagen film to a required thickness. This composite is then blast frozen. Collagen slurry and film layers can be built up to any desired thickness by this procedure. It is also possible, but less convenient, to layer collagen film onto unfrozen collagen slurry followed by a second layer of unfrozen collagen slurry.

In a variant, oxidized regenerated cellulose is obtained commercially in the form of SURGICEL™ fabric and is pre-coated with hyaluronic acid (1% solution in water) and re-dried in warm air. This material is used as the uppermost lamina in a sponge film laminated structure made as described above. An advantage of this material is found to be that it can be sutured into place in the wound bed, the SURGICEL™ providing strength to hold the sutures.

EXAMPLE 4

The rates of release of chlorhexidine from the sponge of Example 2 and heteromorphic sponges made as in Example 3 are compared as follows.

The heteromorphic sponges used for comparison purposes are two of the sponges made in Example 3. The first comprises two layers of the standard thickness collagen film sandwiched by three layers of collagen sponge. The second comprises two layers of the double thickness collagen film sandwiched by three layers of collagen sponge. Both the collagen films and the collagen sponge incorporate chlorhexidine gluconate as described in Example 3.

The comparison is made by placing pieces of the sponge or the heteromorphic sponge of identical size and shape (1cm×1 cm×0.5 cm) in 20 ml water at 20° C. with stirring and measuring the release of chlorhexidine spectrophotometrically by absorbance at 253 nm.

Surprisingly, it is found that the chlorhexidine is released much more rapidly from the heteromorphic sponges of Example 3 than from the isomorphic sponge of Example 2. The time required to release 50% of the chlorhexidine from the heteromorphic sponges is approximately 5 minutes for the heteromorphic sponge, as compared with 15–20 minutes for the isomorphic sponge.

The above examples are intended by way of illustration only. Other embodiments of the present invention falling within the scope of the accompanying claims will be apparent to the skilled reader.

We claim:

1. A method of making a bioabsorbable heteromorphic sponge for use in promoting wound healing, the method comprising the steps of:

adding a pharmacologically active agent to one of a first biopolymer component or at least one second biopolymer component;

forming a heterogeneous premix comprising the first biopolymer component and the second biopolymer component dispersed in a liquid; and freeze-drying the heterogeneous premix to form the heteromorphic sponge wherein said first biopolymer forms a matrix of sponge and said second biopolymer forms a macroscopic substructure within the matrix of the first biopolymer and wherein said matrix and said substructure provide for phased release of said pharmacologically active agent.

2. The method of claim 1 wherein the at least one second biopolymer component is in a form selected from the group consisting of milled freeze-dried sponges, powders, films, flaked or broken films, aggregates, microspheres, fibres, fibre bundles and mixtures thereof.

3. The method of claim 1 wherein the first biopolymer component and the said at least one second bipolymer component comprise biopolymers selected from the group consisting of collagen, elastin, fibronectin, vitronectin, laminin, tenascin, hyaluronic acid, chondroitin sulphate, dermatan sulphate, heparan sulphate, fibrin, oxidised regenerated cellulose, dextran and mixtures thereof.

4. The method of claim 1 wherein the pharmacologically active agent is selected from the group consisting of antimicrobials, cytokines, growth factors, growth factor antagonists, antibodies, peptides, angiogenic factors, hormones, enzymes, metabolic or breakdown products of biopolymers, pain killers and mixtures thereof.

5. The method of claim 1 wherein the liquid comprises water.

6. The method of claim 1, wherein the heterogeneous premix is a gel, paste, slurry or emulsion.

7. The method of claim 1 wherein the heterogeneous premix further contains dissolved acid in an amount sufficient to provide a pH of the heterogeneous premix between 2 and 6.

* * * * *